United States Patent [19]

Sunder et al.

[11] 4,254,125
[45] Mar. 3, 1981

[54] 2-CHLORO-3-PHENOXYPYRAZINES AND 2-CHLORO-6-PHENOXYPYRAZINES POSSESSING ANTIVIRAL ACTIVITY

[75] Inventors: Shyam Sunder; John K. Daniel; Norton P. Peet, all of Indianapolis, Ind.

[73] Assignee: The Dow Chemical Company, Midland, Mich.

[21] Appl. No.: 137,662

[22] Filed: Apr. 7, 1980

[51] Int. Cl.³ .................. A61K 31/495; C07D 241/16
[52] U.S. Cl. .................................. 424/250; 544/405; 544/408; 544/409
[58] Field of Search ................. 544/408, 405; 424/250

[56] References Cited

U.S. PATENT DOCUMENTS

| | | | |
|---|---|---|---|
| 3,452,016 | 6/1969 | Horne | 544/408 |
| 3,501,472 | 3/1970 | Wilcox et al. | 544/408 |
| 3,940,392 | 2/1976 | Johnston | 544/408 |

*Primary Examiner*—Donald G. Daus
*Assistant Examiner*—James H. Turnipseed

[57] ABSTRACT

A series of 2-chloro-3-phenoxypyrazines and 2-chloro-6-phenoxypyrazines exhibiting antiviral activity are disclosed. Methods of using the disclosed compounds as antiviral agents are also described as well as pharmaceutically-acceptable compositions.

33 Claims, No Drawings

2-CHLORO-3-PHENOXYPYRAZINES AND 2-CHLORO-6-PHENOXYPYRAZINES POSSESSING ANTIVIRAL ACTIVITY

SUMMARY OF THE INVENTION

The present invention is directed to compounds of the formula:

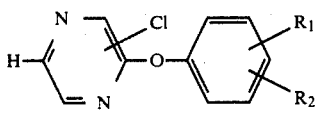

wherein $R_1$ and $R_2$ each independently represent hydrogen, lower alkyl, lower alkoxy, nitro, amino, cyano, trifluoromethyl, acetyl, methylthio, methylsulfinyl, methylsulfonyl, aminosulfonyl, phenoxy or halogen; or alternatively $R_1$ and $R_2$ taken together represent methylenedioxy.

As used in the specification and claims, the term "halogen" represents bromo, chloro or fluoro; "lower alkyl" represents an alkyl group having from 1 to 3 carbon atoms, such as methyl, ethyl, propyl or isopropyl, and "lower alkoxy" represents an alkoxy group having from 1 to 3 carbon atoms, such as methoxy, ethoxy, propoxy or isopropoxy.

Preferred subject compounds are those compounds represented by formula I in which $R_1$ and $R_2$ each independently represent chloro, cyano, hydrogen, phenoxy or nitro.

For convenience, the compounds of the present invention are often referred to herein as "subject compounds," it being understood that information pertaining to activity, preparation, use, etc. is applicable to both 2-chloro-3-phenoxypyrazine and 2-chloro-6-phenoxypyrazine compounds unless reference is specifically made to either the 2-chloro-3-phenoxypyrazine compounds or the 2-chloro-6-phenoxypyrazine compounds.

The compounds disclosed herein exhibit antiviral activity and thus can be used to inhibit viruses by contacting a virus and preferably, virus host cell with an effective amount of the appropriate subject compound. The present invention is further directed to methods of using the compounds of the invention as antiviral agents in which a virus or virus host cell (i.e., a cell susceptible to infection by the virus) is contacted with an effective amount of one or more of the subject compounds. The present invention is also directed to antiviral compositions which can contain from about 5 micrograms (μg) or less of active compound per milliliter (ml) of carrier to about 99 percent (%) by weight of the active compound in combination with a pharmaceutically-acceptable carrier.

DETAILED DESCRIPTION OF THE INVENTION

The compounds of the present invention are prepared by reacting a phenol having the general formula:

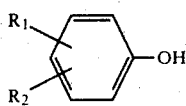

wherein $R_1$ and $R_2$ have the same definitions as previously described herein, with 2,3-dichloropyrazine (when the desired subject compound is a 2-chloro-3-phenoxypyrazine) or with 2,6-dichloropyrazine (when the desired subject compound is a 2-chloro-6-phenoxypyrazine) in a suitable solvent, generally a lower alkanol such as ethanol or isopropanol, in the presence of a suitable base, such as sodium hydroxide. Other suitable base/solvent systems are, for example, sodium hydroxide/isopropanol, sodium ethoxide/ethanol and potassium hydroxide/ethanol.

The reactants are contacted and mixed and the resulting reaction mixture refluxed for a time sufficient to obtain the desired subject compound.

In addition, the subject compounds are prepared using sodium metal with an organic solvent such as benzene or toluene. In this procedure, the appropriate phenol, sodium metal and organic solvent are mixed and refluxed until the phenate is formed, whereupon 2,3-dichloropyrazine or 2,6-dichloropyrazine is added and the resulting mixture refluxed for a time sufficient to obtain the desired 2-chloro-3-phenoxypyrazine or 2-chloro-6-phenoxypyrazine.

Usually, the subject compounds can be separated from the reaction mixture and purified utilizing techniques well known in the art such as organic solvent extraction, filtration, centrifugation, distillation at reduced pressure and recrystallization. Usually, the separation is accomplished as follows. The reaction mixture is cooled and then concentrated and the resulting concentrate poured into water, resulting in the precipitation of a solid or the separation of an oil. When a precipitate is formed, the precipitate is removed by filtration or centrifugation, dried and then recrystallized, if necessary, to give the desired product.

When an oil is formed, the oil can be extracted using a suitable organic solvent such as methylene chloride. The organic solvent is washed with a saturated sodium chloride solution, dried over sodium sulfate and the organic solvent evaporated leaving a solid or oil which can be purified, if necessary, using conventional methodology.

The following examples illustrate the invention but are not to be construed as a limitation thereon.

EXAMPLE 1

2-Chloro-3-(3-(trifluoromethyl)phenoxy)pyrazine

In a 250-milliliter (ml) single-necked, round-bottomed flask containing a solution of 3.0 grams (g) (75 millimoles (mmol) of sodium hydroxide in 100 ml of absolute ethanol was added 11.2 g (66.6 mmol) of 3-(trifluoromethyl)phenol. To this solution was then added 10.0 g (66 mmol) of 2,3-dichloropyrazine and the resulting bright yellow solution refluxed for 72 hours. After cooling, the reaction mixture was concentrated by rotary evaporation and the concentrate poured into approximately 250 ml of water resulting in the formation of an oil which was taken up in methylene chloride. The layers were separated and the methylene chloride layer washed with a saturated sodium chloride solution. The methylene chloride layer was then dried over sodium sulfate and concentrated by rotary evaporation to give 18.1 g of a light yellow liquid. Immersion of the liqht yellow liquid into a dry ice/isopropanol bath induced crystallization and the resulting solids were recovered by filtering. Recrystallization from absolute ethanol gave 6.6 g (36% yield) of the product, 2-chloro-3-(3-

(trifluoromethyl)phenoxy)pyrazine, as white flakes having a melting point (mp) of 69°–71° C.

Elemental analysis found carbon 47.90 percent, hydrogen 2.26 percent and nitrogen 10.36 percent, as compared to calculated values of carbon 48.10 percent, hydrogen 2.20 percent and nitrogen 10.20 percent.

EXAMPLE 2

2-Chloro-3-(3-nitrophenoxy)pyrazine

In a 250-ml single-necked, round-bottomed flask containing a solution of 3.0 g (75 mmol) of sodium hydroxide in 100 ml of absolute ethanol was added 9.28 g (67 mmol) of 3-nitrophenol at which point the solution turned dark red. To the dark red solution, 10.0 g (66 mmol) of 2,3-dichloropyrazine was added and the resulting solution refluxed for 162 hours. The reaction mixture was cooled and concentrated. Upon pouring the concentrate into approximately 300 ml of water, an off-white solid precipitated which was collected by filtration. Recrystallization from absolute ethanol gave the product, 2-chloro-3-(3-nitrophenoxy)pyrazine, (46% yield) as white needles, mp 119°–121° C.

Elemental analysis found carbon 48.0 percent, hydrogen 2.59 percent and nitrogen 16.58 percent, as compared to calculated values of carbon 47.73 percent, hydrogen 2.40 percent and nitrogen 16.70 percent.

EXAMPLE 3

2-Chloro-3-(3-chlorophenoxy)pyrazine

To a solution of 2.7 g (68 mmol) of sodium hydroxide in 100 ml of absolute ethanol was added 8.61 g (67 mmol) of 3-chlorophenol. After solution was achieved, 10.0 g (66 mmol) of 2,3-dichloropyrazine was added and the resulting mixture refluxed for 89 hours. Following reflux, the solution was concentrated by rotary evaporation and then poured into approximately 250 ml of water resulting in the formation of an oil. The material was extracted with methylene chloride (three times using 100 ml of methylene chloride) and the extracts washed with a saturated sodium chloride solution. The methylene chloride layer was dried over sodium sulfate and concentrated using a rotary evaporator leaving 17.0 g of a clear, colorless oil which crystallized upon standing. Recrystallization from hexane gave 5.85 g (36% yield) of the product, 2-chloro-3-(3-chlorophenoxy)-pyrazine, as fine white needles, mp 83°–85° C.

Elemental analysis found carbon 50.0 percent, hydrogen 2.63 percent and nitrogen 11.55 percent, as compared to calculated values of carbon 49.82 percent, hydrogen 2.51 percent and nitrogen 11.62 percent.

EXAMPLE 4

2-(1,3-Benzodioxol-5-yloxy)-3-chloropyrazine

In a single-necked 250-ml round-bottomed flask containing a stirred mixture of 0.633 g (27.5 milligram-atoms) of sodium and 50 ml of benzene was added 19 g (0.137 mol) of sesamol. The resulting mixture was refluxed for one hour until the phenate had entirely formed. At this time, 4.10 g (27.5 mmol) of 2,3-dichloropyrazine was added and the resulting solution refluxed for seven hours. After reflux, the reaction mixture was concentrated and the concentrate poured in 750 ml of 2 N sodium hydroxide solution. The sodium hydroxide solution was then extracted three times with 125-ml portions of diethyl ether. The extract was washed with saturated sodium chloride solution and dried over sodium sulfate. Rotary evaporation of the extract gave a yellow residue which crystallized upon being refrigerated. Upon trituration with methanol, a light tan crystalline solid was obtained. Filtration gave 0.5 g (7% yield) of the product, 2-(1,3-benzodioxol-5-yloxy)-3-chloropyrazine, as a light-tan powder, mp 87°–88° C.

Elemental analysis found carbon 52.6 percent, hydrogen 2.88 percent and nitrogen 11.32 percent, as compared to calculated values of carbon 52.71 percent, hydrogen 2.82 percent and nitrogen 11.18 percent.

EXAMPLE 5

2-Chloro-3-(4-methoxyphenoxy)pyrazine

To 3.0 g (75 mmol) of sodium hydroxide in 100 ml of absolute ethanol was added 8.31 g (67 mmol) of 4-methoxyphenol. To this orange solution was added 10.0 g (66 mmol) of 2,3-dichloropyrazine and the resulting reaction mixture refluxed for 63 hours. After reflux, the reaction mixture was cooled, then concentrated and the concentrate poured into water whereupon an oil was formed. The material was extracted three times with 100 ml of methylene chloride. The methylene chloride extract was washed with saturated sodium chloride, dried over sodium sulfate and rotary evaporated to give 16.76 g of a light yellow liquid. The light yellow liquid was distilled and a white solid obtained from the second fraction (115°–119° C./0.4 millimeters (mm) of mercury). After washing the solid with methanol, 3.75 g (24% yield) of the product, 2-chloro-3-(4-methoxyphenoxy)pyrazine, was obtained as a white crystalline solid, mp 62°–64° C.

Elemental analysis found carbon 56.06 percent, hydrogen 3.89 percent and nitrogen 11.89 percent, as compared to calculated values of carbon 55.82 percent, hydrogen 3.83 percent and nitrogen 11.84 percent.

EXAMPLE 6

2-Chloro-3-(4-phenoxyphenoxy)pyrazine

To a solution of 3.0 g (75 mmol) of sodium hydroxide in 100 ml of absolute ethanol was added 12.48 g (66 mmol) of 4-phenoxyphenol. To this solution was added 10.0 g (66 mmol) of 2,3-dichloropyrazine and the resulting solution refluxed for 135 hours. The cooled reaction mixture was concentrated and the concentrate poured into water. The aqueous mixture was extracted with methylene chloride. The methylene chloride layer was washed with a saturated sodium chloride solution, dried over sodium sulfate and concentrated, leaving 15.4 g of a viscous light yellow oil.

The visous oil was distilled and a solid obtained from the third fraction (165°–170° C./0.2 mm of mercury), which was recrystallized from ethanol to give 5.85 g (30% yield) of the product, 2-chloro-3-(4-phenoxyphenoxy)pyrazine, as a white powder, mp 53°–55° C.

Elemental analysis found carbon 64.5 percent, hydrogen 3.81 percent and nitrogen 9.47 percent, as compared to calculated values of carbon 64.33 percent, hydrogen 3.71 percent and nitrogen 9.38 percent.

Other 2-chloro-3-phenoxypyrazines falling within the scope of the present invention were prepared in essentially the same manner as previously described herein. These compounds are described in Table 1.

TABLE 1

| Compound Example Number | Compound Name | % Yield | mp, °C. | Calculated % C | H | N | Found % C | H | N |
|---|---|---|---|---|---|---|---|---|---|
| 7 | 2-Chloro-3-(4-cyanophenoxy)pyrazine | 18 | 115–118 | 57.03 | 2.61 | 18.14 | 57.3 | 2.75 | 18.27 |
| 8 | 2-Chloro-3-(3-phenoxyphenoxy)pyrazine | 25 | 73–75 | 64.33 | 3.71 | 9.38 | 64.2 | 3.88 | 9.48 |
| 9 | 2-Chloro-3-(4-chlorophenoxy)pyrazine | 20 | 88–91 | 49.82 | 2.51 | 11.62 | 50.1 | 2.71 | 11.44 |
| 10 | 2-Chloro-3-(3-cyanophenoxy)pyrazine | 38 | 119–121 | 57.03 | 2.61 | 18.14 | 56.8 | 2.64 | 18.30 |
| 11 | 2-Chloro-3-(3-methoxyphenoxy)pyrazine | 43 | 57–60 | 55.82 | 3.83 | 11.84 | 55.8 | 3.82 | 11.96 |
| 12 | 2-Chloro-3-(4-nitrophenoxy)pyrazine | 21 | 131–133 | 47.73 | 2.40 | 16.70 | 47.6 | 2.56 | 16.85 |

EXAMPLE 13

2-Chloro-6-(4-chlorophenoxy)pyrazine

To 2.4 g of finely cut sodium metal in 150 ml of absolute ethanol was added 12.86 g of 4-chlorophenol and the mixture stirred for 5 minutes. To the above described mixture, 14.89 g of 2,6-dichloropyrazine was added and this mixture refluxed for 32 hours. After reflux, the reaction mixture was concentrated and the residue poured into water. The resulting aqueous mixture was made slightly basic and then extracted with methylene chloride. The methylene chloride layer was dried over sodium sulfate and then evaporated leaving a solid. Recrystallization from ethanol/water gave 11.4 g (47% yield) of the product, 2-chloro-6-(4-chlorophenoxy)pyrazine, as colorless crystals, mp 92°–93° C.

Elemental analysis found carbon 49.8%, hydrogen 2.56% and nitrogen 11.78% as compared to calculated values of carbon 49.82%, hydrogen 2.51% and nitrogen 11.62%.

EXAMPLE 14

2-Chloro-6-(4-cyanophenoxy)pyrazine

A mixture of 14.9 g (0.100 mole) of 2,6-dichloropyrazine, 11.9 g of 4-cyanophenol and 4.40 g (0.110 mole) of sodium hydroxide in 100 ml of absolute ethanol was refluxed for 48 hours. The reaction mixture was concentrated and the residue poured into water. The resulting aqueous mixture was extracted with methylene chloride and the methylene chloride layer was dried over sodium sulfate and evaporated to leave 9.3 g of crude product. Recrystallization from ethanol gave 8.1 g (35% yield) of the product, 2-chloro-6-(4-cyanophenoxy)pyrazine, as colorless crystals, mp 126°–128° C.

Elemental analysis found carbon 57.2%, hydrogen 2.71% and nitrogen 18.19% as compared to calculated values of carbon 57.03%, hydrogen 2.61% and nitrogen 18.14%.

EXAMPLE 15

2-Chloro-6-(4-nitrophenoxy)pyrazine

A mixture of 1.489 g of 2,6-dichloropyrazine, 13.9 g of 4-nitrophenol and 4.4 g of sodium hydroxide in 150 ml of ethanol was refluxed for 48 hours. The reaction mixture was concentrated and the residue poured into water whereupon a precipitate formed. The precipitate was removed by filtration and the solid obtained twice recrystallized from ethanol which gave 3.1 g (12% yield) of the product, 2-chloro-6-(4-nitrophenoxy)pyrazine, as colorless crystals, mp 125°–127° C.

Elemental analysis found carbon 47.8%, hydrogen 2.57% and nitrogen 16.91% as compared to calculated values of carbon 47.73% hydrogen 2.40% and nitrogen 16.70%.

EXAMPLE 16

2-Chloro-6-(3-nitrophenoxy)pyrazine

A mixture of 14.8 g of 2,6-dichloropyrazine, 13.9 g of 3-nitrophenol and 4.4 g of sodium hydroxide in 150 ml of ethanol was refluxed for 32 hours. The reaction mixture was concentrated and poured into water. The resulting mixture was made basic with sodium hydroxide and extracted with methylene chloride. The methylene chloride layer was dried over sodium sulfate and then evaporated leaving a solid. Recrystallization from ethanol-water/charcoal gave 11.2 g (44.5%) of the product, 2-chloro-6-(3-nitrophenoxy)pyrazine, mp 118°–119° C.

Elemental analysis found carbon 47.9%, hydrogen 2.37% and nitrogen 16.86% as compared to calculated values of carbon 47.73%, hydrogen 2.40% and nitrogen 16.70%.

Other 2-chloro-6-phenoxypyrazines within the scope of the invention were prepared in essentially the same manner as described herein, these compounds are described in Table 2.

TABLE 2

| Compound Example Number | Compound Name | % Yield | Bp, °C./mm* mp, °C. | Calculated % C | H | N | Found % C | H | N |
|---|---|---|---|---|---|---|---|---|---|
| 17 | 2-Chloro-6-(4-phenoxyphenoxy)pyrazine | 43 | 58–59 | 64.33 | 3.71 | 9.38 | 64.14 | 3.74 | 19.50 |
| 18 | 2-Chloro-6-(3-methoxyphenoxy)pyrazine | 16 | 125–127/0.1 mm | 55.82 | 3.83 | 11.84 | 56.00 | 3.85 | 11.99 |
| 19 | 2-Chloro-6-(3-cyanophenoxy)pyrazine | 48 | 107–109 | 57.03 | 2.61 | 18.14 | 57.3 | 2.74 | 18.29 |
| 20 | 2-Chloro-6-(3-phenoxyphenoxy)pyrazine | 81 | 135–140/0.2 mm | 64.33 | 3.71 | 9.38 | 64.6 | 3.83 | 9.55 |
| 21 | 2-Chloro-6-(3-(trifluoromethyl)phenoxy)pyrazine | 49 | 97–99/0.3 mm | 48.10 | 2.20 | 10.20 | 48.2 | 2.32 | 10.43 |
| 22 | 2-Chloro-6-(4-methoxyphenoxy)pyrazine | 69 | 120–122/0.2 mm | 55.82 | 3.83 | 11.84 | 56.0 | 3.90 | 12.16 |
| 23 | 2-Chloro-6-(3-chlorophenoxy)pyrazine | 51 | 75/0.5 mm | 49.82 | 2.51 | 11.62 | 49.80 | 2.64 | 11.84 |
| 24 | 2-Chloro-6-(1,3-benzodioxol-5-yloxy)-pyrazine | 51 | 92–93 | 52.71 | 2.82 | 11.18 | 52.9 | 2.73 | 11.30 |

*"Bp. °C./mm" refers to those compounds recovered by distillation at reduced pressure and indicates the boiling point in degrees Centigrade at the stated pressure, indicated in millimeters of mercury, and "mp. °C." represents the melting point in degrees Centigrade for those compounds in which the melting point was determined.

Antiviral activity for the subject compounds was demonstrated utilizing the following tissue culture testing procedure.

Monolayered HeLa cells in 16 millimeter (mm) tissue culture dishes were treated with 1 ml of culture medium (Eagles medium supplemented with fetal calf serum) containing compound at 100, 50, 25, 12.5, 6.25 or 0 µg/ml. Culture media such as those described herein are more fully described in standard texts, as for example, Kuchler's Biochemical Methods in Cell Culture and Virology, Dowden, Hutchinson and Ross, Inc., Stroudsberg, PA (1977). Immediately following treatment, cells were challenged with 0.05 ml of rhinovirus type 1A (RV-1A), rhinovirus type 2 (RV-2) or coxsackie $A_{21}$ virus (Cox $A_{21}$) in culture medium. Cell controls received no virus. Cultures were observed for compound cytotoxicity and viral cytopathic effect (CPE) at 48 and 72 hours post-treatment.

Some of the subject compounds were also tested in animals as follows.

Swiss male mice, 10–12 grams in weight, were challenged intraperitoneally (IP) with 0.2 ml of a normally lethal dose, i.e., 5 to 10 times the dosage required to kill 50 percent of the animal population treated (5–10 $LD_{50}$), of Cox $A_{21}$ virus in phosphate buffered saline containing 1 percent heat inactivated fetal calf serum. Three hours later mice were treated IP or orally (PO) with 0.2 ml of compound suspended in 0.5 percent hydroxypropyl methylcellulose (Methocel) or with 0.2 ml of Methocel alone. Compounds administered intraperitoneally were used at a concentration of either 7.5 mg/ml, 10 mg/ml or 20 mg/ml. Thus 0.2 ml of compound suspended in 0.5 percent Methocel represents a dosage of 150 milligrams/kilogram (mg/kg), 200 mg/kg or 400 mg/kg, respectively. The compound administered orally was used at a 30 mg/ml concentration, which is a 600 mg/kg dosage. Mice were counted daily for 7–10 days post-challenge and deaths recorded. A modified Mantel-Haenzel combined chi-square procedure was used to determine significant difference between virus control and treated groups. Chi-square values greater than 3.84 are considered significant (95 percent confidence level) in this test. Test results are shown in Table 3.

TABLE 3

| Compound Example No. | Cytotoxicity* (µg/ml) | Tissue Culture Testing**(µg/ml) | | | Animal Testing | | | |
|---|---|---|---|---|---|---|---|---|
| | | | | | IP | | PO | |
| | | RV-1A | RV-2 | Cox $A_{21}$ | Dose (mg/kg) | $X^2$ | Dose (mg/kg) | $X^2$ |
| 1 | 100 | 25 | 25 | 50 | | | | |
| 2 | >100 | 12.5 | 25 | 50 | 200 | 6.07 | | |
| 3 | 100 | 12.5 | 12.5 | 50 | 200 | 0.028 | | |
| 4 | 100 | 100 | 25 | 25 | | | | |
| 5 | 100 | 50 | 25 | 100 | | | | |
| 6 | 50 | 25 | 12.5 | 6.25 | 400 | 7.965 | 600 | 1.301 |
| 7 | ≧100 | 50 | 25 | 25 | | | | |
| 8 | >100 | NA | 25 | 6.25 | 400 | 12.861 | | |
| 9 | 100 | 12.5 | 12.5 | 100 | 200 | 0.208 | | |
| 10 | 100 | 25 | 12.5 | ≧100 | | | | |
| 11 | 100 | 50 | 50 | 12.5 | | | | |
| 12 | >100 | 100 | 100 | NA | 200 | 0.147 | | |
| 13 | >100 | 50 | 50 | 12.5 | 400 | 17.359 | 600 | 4.486 |
| 14 | 100 | 25 | 12.5 | 6.25 | 150 | 4.536 | | |
| 15 | >100 | 25 | 6.25 | 6.25 | 400 | 24.456 | 600 | 9.042 |
| 16 | >100 | 6.25 | 25 | 50 | 400 | 5.926 | 600 | 8.099 |
| 17 | 50 | 6.25 | ≦6.25 | <6.25 | 400 | 2.484 | 600 | 1.356 |
| 18 | 50 | NA | 50 | NA | 400 | 1.486 | | |
| 19 | 100 | 6.25 | 50 | 50 | 150 | 0.062 | | |
| 20 | 50 | 25 | 6.25 | 6.25 | 400 | 1.523 | | |
| 21 | 50 | 6.25 | 50 | 50 | 400 | 0.368 | | |
| 22 | 50 | 25 | 25 | 6.25 | 400 | 1.917 | | |
| 23 | 50 | 6.25 | 50 | 50 | 400 | 0.551 | | |
| 24 | ≧100 | 25 | 12.5 | 25 | 400 | 1.124 | | |

*Cytotoxicity figures represent the concentration of compound (µg/ml) found to be toxic to the cell.
**Lowest concentration of compound (µg/ml) necessary to cause a 50 percent reduction in cytopathic effect. The symbol "NA" indicates that the compound was not active against that particular virus at the standard test conditions; "<" means "less than"; "≦" means "less than or equal to"; ">" means "greater than" and "≧" means "greater than or equal to".

The data in Table 3 demonstrates the antiviral activity of representative compounds falling within the scope of the present invention. The tissue culture test data indicates that all the tested compounds are active against at least one of the three test viruses (RV-1A, RV-2 or Cox $A_{21}$). In addition, compound Example Nos. 2, 6, 8, 13, 14, 15 and 16 (at the 95 percent confidence level) show that they are active antiviral compounds in at least one of the animal tests.

In using the compounds of the invention, a virus or virus host cell is contacted with an amount of one or more of the compounds effective to inhibit the virus. Although the invention should not be construed as limited to any particular theory of action, it appears that the compounds act to inhibit virus in host cells, rather than by direct chemical or physical inactivation of the virus particle apart from the cell. In antiviral applications carried out in non-living environments, contacting should be carried out in a manner effective to ensure continued presence of an effective amount of the compound when subsequent contact with host cells occurs. Preferably, the compounds are used by contacting the host cells with an effective antiviral amount (i.e., the amount which must be employed to achieve significant viral inhibition) of one or more of the compounds. The contacting can be carried out directly, as by addition of the compound to cells in tissue culture, to inhibit contaminating viruses. Contacting can also be carried out by administering an antiviral dosage of a compound of the invention to an animal (preferably such animal is a mammal). The compounds can be administered to animals parenterally (for example, by intraperitoneal, subcutaneous or intravenous injection) or orally, and the oral antiviral activity of certain of the compounds is a feature of the invention. In such applications, an effective antiviral dose of one or more of the compounds is administered to an animal. Selection of the compound or compounds for administration to animals in particular cases is dictated by considerations such as toxicity, mutagenicity, ease of administration, antiviral activity (potency), stability, compatibility with suitable carriers, etc.

The exact amount of the compound or compounds to be employed, i.e., the amount of the subject compound or compounds sufficient to provide the desired effect, depends on various factors such as the compound employed; type of contacting or administration; the size, age and species of animal; the route, time and frequency of administration; the virus or viruses involved, and whether or not the compound is administered prophylactically or is administered to an infected animal to inhibit the infecting virus. In particular cases, the amount to be administered can be ascertained by conventional range finding techniques, for example, by observing the effect produced at different rates using conventional virus assay procedures.

The compounds are preferably administered in the form of a composition comprising the compound in admixture with a pharmaceutically-acceptable carrier, i.e., a carrier which is chemically inert to the active compound and which has no detrimental side effects or toxicity under the conditions of use. As shown above, the compounds when administered to tissue culture medium exhibit significant antiviral activity at low concentrations, as for example, the finding that a concentration of 6.25 µg/ml or less of a subject compound was often sufficient to cause a 50% reduction in cytopathic effect against a particular test virus in the tissue culture testing.

Such compositions can contain from about 5 micrograms or less of the active compound per milliliter of carrier to about 99 percent by weight of the active compound in combination with a pharmaceutically-acceptable carrier.

Preferred compositions include compositions containing from about 5 µg of active compound per milliliter of carrier to about 0.0025 to about 0.05 to about 0.25 to about 0.5 to about one to about 10 to about 25 to about 50 percent by weight of active compound in a pharmaceutically-acceptable carrier.

The compositions can be in solid forms such as tablets, capsules, granulations, feed mixes, feed supplements and concentrates, powders, granules or the like; as well as liquid forms such as sterile injectable suspensions, orally administered suspensions, or solutions. The pharmaceutically-acceptable carriers can include excipients such as surface-active dispersing agents, suspending agents, tableting binders, lubricants, flavors and colorants. Suitable excipients are disclosed, for example, in texts such as Remington's Pharmaceutical Manufacturing, Thirteenth Edition, Mack Publishing Co., Easton, PA (1965).

What is claimed is:

1. A compound of the formula:

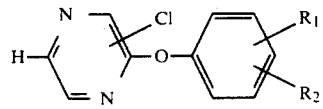

wherein $R_1$ and $R_2$ each independently represent hydrogen, lower alkyl, lower alkoxy, nitro, amino, cyano, trifluoromethyl, acetyl, methylthio, methylsulfinyl, methylsulfonyl, aminosulfonyl, phenoxy or halogen; or alternatively $R_1$ and $R_2$ taken together represent methylenedioxy.

2. The compound of claim 1 wherein $R_1$ and $R_2$ each independently represent chloro, cyano, hydrogen, phenoxy or nitro.

3. The compound of claim 1 which is 2-chloro-3-(3-(trifluoromethyl)phenoxy)pyrazine.

4. The compound of claim 1 which is 2-chloro-3-(3-nitrophenoxy)pyrazine.

5. The compound of claim 1 which is 2-chloro-3-(3-chlorophenoxy)pyrazine.

6. The compound of claim 1 which is 2-(1,3-benzodioxol-5-yloxy)-3-chloropyrazine.

7. The compound of claim 1 which is 2-chloro-3-(4-methoxyphenoxy)pyrazine.

8. The compound of claim 1 which is 2-chloro-3-(4-phenoxyphenoxy)pyrazine.

9. The compound of claim 1 which is 2-chloro-3-(4-cyanophenoxy)pyrazine.

10. The compound of claim 1 which is 2-chloro-3-(3-phenoxyphenoxy)pyrazine.

11. The compound of claim 1 which is 2-chloro-3-(4-chlorophenoxy)pyrazine.

12. The compound of claim 1 which is 2-chloro-3-(3-cyanophenoxy)pyrazine.

13. The compound of claim 1 which is 2-chloro-3-(3-methoxyphenoxy)pyrazine.

14. The compound of claim 1 which is 2-chloro-3-(4-nitrophenoxy)pyrazine.

15. The compound of claim 1 which is 2-chloro-6-(4-chlorophenoxy)pyrazine.

16. The compound of claim 1 which is 2-chloro-6-(4-cyanophenoxy)pyrazine.

17. The compound of claim 1 which is 2-chloro-6-(4-nitrophenoxy)pyrazine.

18. The compound of claim 1 which is 2-chloro-6-(3-nitrophenoxy)pyrazine.

19. The compound of claim 1 which is 2-chloro-6-(4-phenoxyphenoxy)pyrazine.

20. The compound of claim 1 which is 2-chloro-6-(3-methoxyphenoxy)pyrazine.

21. The compound of claim 1 which is 2-chloro-6-(3-cyanophenoxy)pyrazine.

22. The compound of claim 1 which is 2-chloro-6-(3-phenoxyphenoxy)pyrazine.

23. The compound of claim 1 which is 2-chloro-6-(3-(trifluoromethyl)phenoxy)pyrazine.

24. The compound of claim 1 which is 2-chloro-6-(4-methoxyphenoxy)pyrazine.

25. The compound of claim 1 which is 2-chloro-6-(3-chlorophenoxy)pyrazine.

26. The compound of claim 1 which is 2-chloro-6-(1,3-benzodioxol-5-yloxy)pyrazine.

27. A method for inhibiting viruses which comprises contacting viruses or virus host cells with an effective virus inhibiting amount of a compound corresponding to the formula:

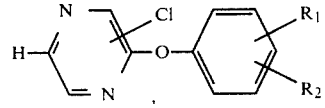

wherein $R_1$ and $R_2$ each independently represent hydrogen, lower alkyl, lower alkoxy, nitro, amino, cyano, trifluoromethyl, acetyl, methylthio, methylsulfinyl, methylsulfonyl, aminosulfonyl, phenoxy or halogen; or alternatively $R_1$ and $R_2$ taken together represent methylenedioxy.

28. The method of claim 27 wherein $R_1$ and $R_2$ each independently represent chloro, cyano, hydrogen, phenoxy or nitro.

29. A method useful for inhibiting viruses which comprises administering to an animal an effective virus inhibiting amount of a compound corresponding to the formula:

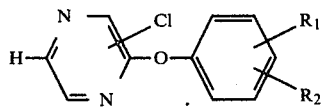

wherein $R_1$ and $R_2$ each independently represent hydrogen, lower alkyl, lower alkoxy, nitro, amino, cyano, trifluoromethyl, acetyl, methylthio, methylsulfinyl, methylsulfonyl, aminosulfonyl, phenoxy or halogen; or alternatively $R_1$ and $R_2$ taken together represent methylenedioxy.

30. The method of claim 29 wherein the animal is infected by virus.

31. The method of claim 29 wherein $R_1$ and $R_2$ each independently represent chloro, cyano, hydrogen, phenoxy or nitro.

32. A virus inhibiting composition comprising a pharmaceutically-acceptable carrier and an effective virus inhibiting amount of a compound corresponding to the formula:

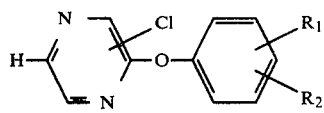

wherein $R_1$ and $R_2$ each independently represent hydrogen, lower alkyl, lower alkoxy, nitro, amino, cyano, trifluoromethyl, acetyl, methylthio, methylsulfinyl, methylsulfonyl, aminosulfonyl, phenoxy or hydrogen; or alternatively $R_1$ and $R_2$ taken together represent methylenedioxy.

33. The composition of claim 32 wherein $R_1$ and $R_2$ each independently represent chloro, cyano, hydrogen, phenoxy or nitro.

* * * * *

UNITED STATES PATENT AND TRADEMARK OFFICE
CERTIFICATE OF CORRECTION

PATENT NO. : 4,254,125
DATED : March 3, 1981
INVENTOR(S) : Shyam Sunder, John K. Daniel and Norton P. Peet It is certified that error appears in the above—identified patent and that said Letters Patent are hereby corrected as shown below:

Column 6, line 16, "1.489" should read --14.89--.

Column 6, Table 2, Compound Example Number 17, under Subtitle N, "19.50" should read --9.50.

Column 12, Claim 32, line 20, "hydrogen;" should read --halogen;--.

Signed and Sealed this

Fourth Day of August 1981

[SEAL]

Attest:

GERALD J. MOSSINGHOFF

Attesting Officer     Commissioner of Patents and Trademarks